United States Patent [19]

Bonnell et al.

[11] Patent Number: 4,628,066
[45] Date of Patent: Dec. 9, 1986

[54] PROCESS FOR THE PRODUCTION OF METHANOL

[75] Inventors: Leo W. Bonnell, Macungie; Joseph M. Pietrantonio, Allentown, both of Pa.

[73] Assignee: Air Products and Chemicals, Inc., Allentown, Pa.

[21] Appl. No.: 828,920

[22] Filed: Feb. 12, 1986

[51] Int. Cl.⁴ .................... C07C 27/06; C07C 31/04
[52] U.S. Cl. .................................. 518/700; 518/704; 518/706; 518/707
[58] Field of Search .............. 518/700, 706, 707, 704

[56] References Cited

U.S. PATENT DOCUMENTS

| 1,868,096 | 7/1932 | Dreyfus . | |
|---|---|---|---|
| 3,326,956 | 6/1967 | Davies et al. | 260/449.5 |
| 3,888,896 | 6/1975 | Espino et al. | 260/449.5 |
| 3,923,694 | 12/1975 | Cornthwaite | 252/463 |
| 4,031,123 | 6/1977 | Espino et al. | 260/449.5 |
| 4,235,799 | 11/1980 | Wentworth et al. | 260/449.5 |
| 4,346,179 | 8/1982 | Sugier et al. | 518/707 |

FOREIGN PATENT DOCUMENTS 1157053  11/1983  Canada ............................ 260/638

*Primary Examiner*—Howard T. Mars
*Attorney, Agent, or Firm*—Mark L. Rodgers; E. Eugene Innis; James C. Simmons

[57] ABSTRACT

The present invention is a process for increasing the capacity of a gas phase synthesis loop for the production of methanol from a syngas feed. The syngas feed is initially passed to a liquid phase methanol reactor to convert a portion of the syngas to methanol or methanol and higher aliphatic alcohols. The mixture is subsequently cooled to condense and recover the methanol and/or higher alcohols. The unreacted syngas is passed to a gas phase synthesis loop for further conversion and recovery of methanol.

13 Claims, 1 Drawing Figure

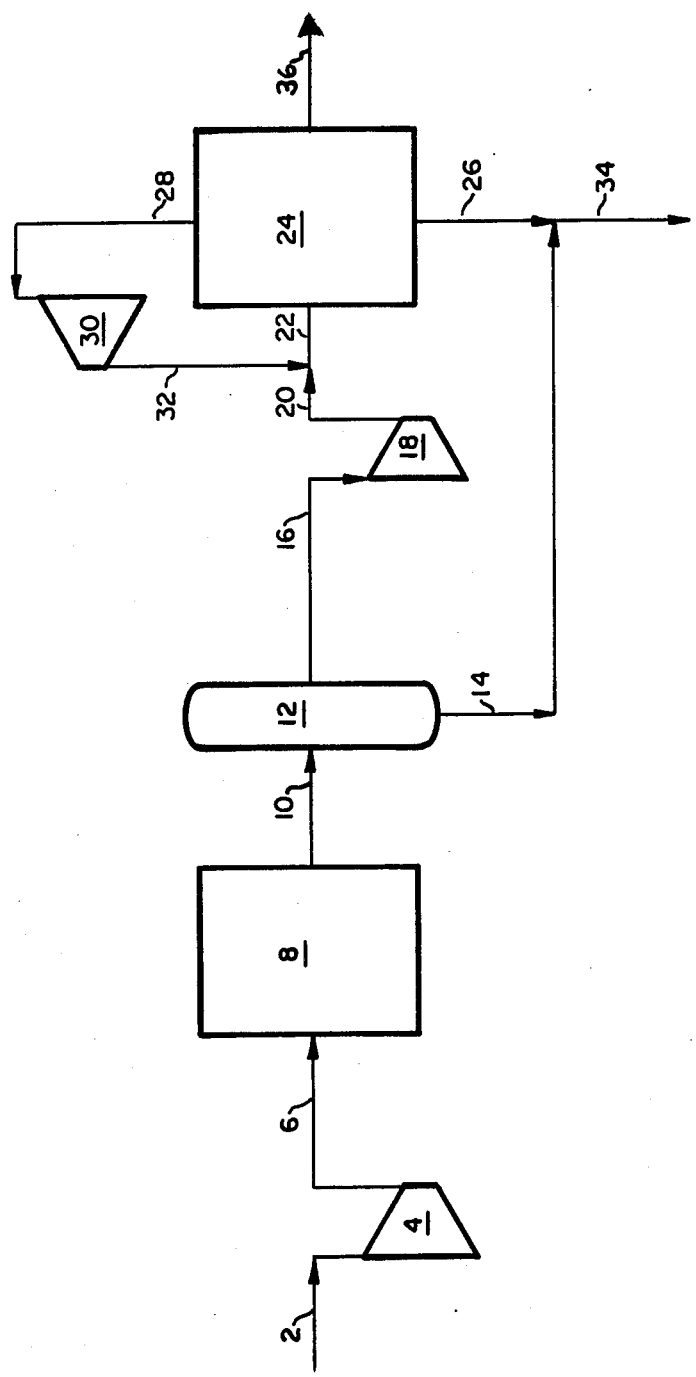

PROCESS FOR THE PRODUCTION OF METHANOL

TECHNICAL FIELD OF THE INVENTION

The present invention relates to the production of methanol or methanol and higher aliphatic alcohols from a syngas feed comprising carbon monoxide and hydrogen.

BACKGROUND OF THE INVENTION

Various methods have been developed for the production of methanol from gas mixtures containing carbon oxides and hydrogen. U.S. Pat. No. 1,868,096 discloses a process for producing methanol by passing a reaction gas mixture under the requisite conditions of temperature and pressure initially over one or more catalyst masses composed of zinc oxide or zinc oxide and chromium oxide and subsequently passing said mixture over one or more methanol catalysts sensitive to sulfur poisoning such as catalysts comprising copper, manganese or compounds of copper or manganese. The reaction gases are passed successively through a number of reaction vessels arranged in series as an open system.

U.S. Pat. No. 4,235,799 discloses a process for producing methanol by passing a mixture of hydrogen and one or more carbon oxides into contact with at least two beds of catalyst arranged in series. The catalyst beds are operated at increasing temperature levels in the direction of flow of the mixture. The mixture is subsequently cooled by indirect heat exchange and passed into contact with at least one further bed of catalyst.

U.S. Pat. No. 4,346,179 discloses a process for producing methanol and its higher homologs from a synthesis gas containing essentially carbon dioxide, carbon monoxide and hydrogen. A synthesis gas is treated in a first catalytic reaction zone at 230°–350° C. The effluent from the first catalytic reaction zone is cooled and condensed and a gas fraction is separated from the liquid condensate. The gas fraction is subsequently treated at 240°–300° C. and a second catalytic reaction zone to produce a liquid methanol fraction. The liquid methanol fraction is subsequently admixed with the liquid condensate to form a gasoline constituent product.

U.S. Pat. No. 3,888,896 discloses a process for producing methanol from carbon monoxide and hydrogen saturating an inert organic liquid medium, such as pseudocumene, with carbon monoxide and hydrogen and contacting the saturated liquid medium with a methanol-forming catalyst such as those containing zinc and chromium.

U.S. Pat. No. 4,031,123 discloses a similar method for preparing methanol with the improvement that paraffinics and cycloparaffinics are used as the inert hydrocarbon liquid in which the catalyst bed is in contact.

Canadian Pat. No. 1,157,053 discloses a liquid phase methanol synthesis process wherein methanol is produced by contacting a synthesis gas comprising hydrogen and carbon monoxide with a catalyst in the presence of an inert liquid. The catalyst in contact with the inert liquid is in the form of particles of a size less than about 125 microns.

BRIEF SUMMARY OF THE INVENTION

The present invention is a process for increasing the capacity; i.e. debottlenecking, a typical gas-phase methanol synthesis loop. A syngas feed, such as a feed from the steam reforming of natural gas, is passed to a liquid phase methanol reactor to convert a portion of the syngas to methanol. The resultant methanol-containing syngas reactor effluent is cooled to condense the methanol, thereby producing a first methanol stream and an unreacted syngas stream. The unreacted syngas stream is passed to a conventional gas-phase methanol synthesis loop to convert at least a portion of the unreacted syngas stream to methanol, thereby forming a second methanol stream. Both the first and second methanol streams are recovered as product or for further processing.

The present invention allows the syngas feed to be passed at an increased flow rate, and at a single pass, through the liquid-phase methanol reactor for partial conversion to methanol, with the unconverted syngas being used as a substitute feed to the gas-phase synthesis loop. This provides a method for increasing the capacity of an existing gas-phase methanol synthesis loop without the extensive equipment modification and cost involved in expanding the gas-phase loop itself. The liquid phase reactor does not contain a recycle loop and therefore can efficiently "debottleneck" an existing system without incurring costly recycle compression requirements. Consequently, the amount of syngas which can be processed in a given period of time can be significantly increased in a manner more economical and efficient than previously thought possible.

The liquid phase methanol reactor can be retrofitted into any typical gas-phase loop which is capable of synthesizing methanol from the syngas feed. The liquid phase reactor typically has a pressure drop of less than about 5 psi, thereby requiring minimal additional compression for the gas-phase synthesis loop feed. An additional advantage of the present process is that, by using various catalysts in the liquid phase reactor, the process can be designed to produce higher aliphatic alcohols as well as methanol as products.

BRIEF DESCRIPTION OF THE DRAWINGS

The single FIGURE is a schematic flow diagram of one embodiment of the present invention.

DETAILED DESCRIPTION OF THE INVENTION

The present invention is a process for increasing the production of methanol from a syngas feed. Typically, methanol is produced from a syngas feed, such as the feed produced from the reforming of natural gas, using a gas-phase methanol synthesis loop. Increasing the capacity of a standard gas-phase methanol loop itself, is difficult and costly due to the high recycle ratios employed; e.g. 8-1 is common, and the high reactor pressure drops. Due to the strong exothermic nature of the methanol synthesis reaction, high recycle ratios are necessary to keep reactor temperatures at acceptable levels. As a result, a proportionate addition of recycle compression capacity, catalysts, reactor volume and heat exchanger surface is necessary to increase the capacity of the synthesis loop, with corresponding high capital costs. Even a small increase in the syngas capacity of the gas-phase loop requires a significant increase in cost.

The present invention increases the capacity of a typical gas-phase methanol loop without many of the drawbacks involved with increasing the loop size itself. Referring to the accompanying FIGURE, a syngas feed stream 2, containing carbon dioxide and hydrogen, is compressed, if necessary, in compressor 4 to form a compressed syngas feed 6 which is passed to a liquid phase methanol reactor 8. The composition of the syngas feed 2 to the liquid phase methanol reactor can be any composition that is an acceptable feed to a conventional gas-phase methanol facility. A typical composition would be 73% $H_2$, 15% CO, 8% $CO_2$, and 4% methane and other inerts, with a preferred stoichiometric ratio $H_2/(CO+1.5\ CO_2)$ between 2–3. Feeds with a stoichiometric ratio outside of this range can be processed, but the efficiency of the system will decrease. For example, if the stoichiometric ratio falls below 2, the unconverted syngas would be difficult to process in the downstream loop because of the hydrogen deficiency.

Typically, the liquid phase methanol reactor operates at a pressure between 400 to 1200 psia, and the syngas feed 2, if not within this pressure range, is compressed in compressor 4. The liquid phase methanol reactor 8 can be any suitable reactor which is capable of converting a portion of the feed gas to methanol. Such reactors are described in U.S. Pat. Nos. 3,888,896 and 4,031,123 and Canadian Pat. No. 1,157,053, all assigned to Chem Systems, Inc. The reactor consists of an active methanol synthesis catalyst suspended in an inert hydrocarbon liquid, usually a mineral oil. The synthesis gas is bubbled through the catalyst-oil mixture where a portion of the $H_2$, CO and $CO_2$ are converted to methanol. Two operating modes can be used: the catalyst can be pellet-sized and fluidized by the inert liquid, or a powdered catalyst can be entrained in the liquid, forming a slurry.

The catalyst used in the liquid phase reactor can be any known methanol-forming catalyst, such as those listed in Column 4 of U.S. Pat. No. 4,031,123. The particle sizes of the catalyst employed are known by those skilled in the art. Average particle sizes may range from 0.00002 to 0.25 inches, depending on the bed type (fixed, fluidized, or slurry) and liquid flow rate. By varying the catalyst composition as well as the reaction conditions in the reactor, higher aliphatic alcohols may be produced along with the methanol. The higher aliphatic alcohols may be condensed and recovered with the methanol as a combined product, or may be separated and recovered as an additional product.

The reactor pressure at the exit can be between 200 psia and 2,000 psia with a preferred range being between 400 psia and 1,000 psia. Below about 400 psia methanol synthesis equilibrium becomes increasingly unfavorable, and condensation of methanol requires costly refrigeration. The reactor temperature can be between 150° C. and 400° C. with best performance between 230° C. and 250° C. Normally, the contents of the reactor vary by only a few degrees C. from top to bottom, or edge to center. The reactor space velocity in units of standard liters (0° C. 1 atm) of feed per hour, per kilogram of catalyst, is preferably between 4000 and 10,000 for the slurry mode of reactor operation with powdered catalyst, and between 2,000 and 6,000 for the fluidized mode with pelletized catalyst.

After partial conversion to methanol, the resultant methanol-containing syngas is removed from contact with the catalyst as stream 10 and the methanol fraction is condensed and separated from the remaining syngas in separator 12. The condensed methanol fraction is removed from the separator as a methanol product stream 14 and the unreacted syngas is removed as stream 16. The unreacted syngas stream 16 is compressed to a pressure between 750 and 3000 psia in compressor 18, to form a compressed syngas stream 20. The compressed syngas stream 20 is combined with a recycle stream 32 to form a combined syngas stream 22 which is passed to a gas-phase synthesis loop facility 24 to convert at least a portion of the syngas to methanol. The gas phase synthesis loop can be any typical gas phase facility common in the art, such as that disclosed in U.S. Pat. Nos. 3,326,956; 3,923,694 and 4,235,799. The methanol synthesized in the gas-phase synthesis loop is removed from the facility as a second methanol product stream 26, and is optionally combined with the first methanol product stream 14 from separator 12 to form a single methanol product stream 34. The unreacted syngas from the gas-phase synthesis loop 24 is removed as stream 28 and compressed to a pressure between 750 and 3000 in compressor 30 to form a compressed syngas stream 32. This compressed syngas stream 32 is recycled and combined with compressed syngas stream 30 entering the gas-phase synthesis loop 24 for further processing. A purge stream 36 is also taken from the synthesis loop.

In the embodiment shown in the accompanying figure, the liquid phase methanol reactor and associated methanol recovery equipment is located intermediate to the two stages of feed gas compression (compressors 4 and 18) for the gas phase synthesis loop. Placing the liquid phase reactor at this point of the process reduces the number of moles of gas that must be fed to the second comprssion stage. Since high single pass conversions are achievable in the liquid phase methanol reactor, the amount of syngas fed to the system can be increased significantly, and hence methanol production increased, without the large cost and equipment increase necessary to reach such capacity with the gas-phase loop alone. Depending upon the circumstances of the application, it may be preferable to place the liquid phase reactor after the second stage of compression, i.e. at a point along stream 16. As the amount of required methanol production for the liquid phase reactor increases, higher pressure requirements become necessary for high conversions due to equilibrium constraints.

The present process scheme allows for an increase in the production of methanol over a traditional methanol synthesis facility, and also provides for an efficient and economical method of increasing the capacity of a conventional gas-phase methanol synthesis loop. Prior attempts to increase the capacity of existing gas-phase loops included frequent replacement of catalyst, building a new, separate loop, and enlarging the existing loop. All of these methods proved unattractive, as the cost associated with each is high when compared to the corresponding increase in capacity achieved.

The liquid phase reactor operates with a high single-pass conversion. The inert liquid in the liquid phase reactor functions as an excellent heat-transfer medium and heat sink, thereby allowing the exothermic methanol synthesis reaction to proceed to a much higher level of conversion of carbon dioxides to methanol without significant temperature rise of the gas and catalyst mass. Such a temperature rise is detrimental to catalyst life and thermodynamic equilibrium, and therefore a limiting factor in a stand alone gas phase system. The high heat capacity of the inert oil relative to the feed gas provides for direct and rapid heating of the gas to synthesis temperatures without the need for feed-product heat exchangers.

Additionally, because a typical liquid phase reactor has a ΔP of less than 5 psi it can be incorporated directly into an existing synthesis gas compression system without the need for a significant increase in compressor size or power.

The following example illustrates one embodiment of the present invention and is not meant to be limiting.

EXAMPLE 1

A computer simulation was developed to establish the effect of retrofitting a liquid phase methanol reactor at the front end of a conventional gas phase synthesis loop. The gas phase loop was designed to produce 2100 metric tons per day (MT/D) of methanol from natural gas without supplemental $CO_2$ addition. The feed is compressed to 490 psi and fed to the liquid phase reactor where about 33% of the CO and 7% of the $CO_2$ is converted to methanol at a 10,000 l/hr-kg space velocity. The reactor effluent is cooled to condense the methanol and the remaining feed is compressed to about 1000 psi and fed to the gas phase synthesis loop for further methanol synthesis.

A heat and material balance for key streams in this process are reported in Table 1 below.

TABLE 1

| Stream Number | 2 | 6 | 14 | 20 | 26 | 32 | 36 |
|---|---|---|---|---|---|---|---|
| Pressure (psia) | 240 | 490 | 460 | 1000 | 862 | 1000 | 90 |
| Temperature (°F.) | 100 | 279 | 92 | 222 | 100 | 130 | 70 |
| Ave. Mol. Wt. | 9.74 | 9.74 | 30.84 | 9.52 | 27.80 | 5.29 | 5.22 |
| Flow Rates Moles/Hr. | | | | | | | |
| Hydrogen | 25,470 | 25,470 | — | 21,420 | 30 | 211,710 | 7,820 |
| Carbon Monoxide | 5,180 | 5,180 | — | 3,440 | — | 4,770 | 180 |
| Carbon Dioxide | 2,710 | 2,710 | 20 | 2,500 | 10 | 3,760 | 140 |
| Methane | 1,290 | 1,290 | — | 1,290 | 20 | 34,030 | 1,270 |
| Nitrogen | 70 | 70 | — | 70 | — | 1,760 | 70 |
| Water | — | — | 210 | — | 2,350 | 130 | 10 |
| Methanol | — | — | 1,830 | 60 | 5,660 | 1,180 | — |
| Ethanol | — | — | 20 | — | 5 | — | — |
| Total Flow | | | | | | | |
| Mole/Hr. | 34,720 | 34,720 | 2,080 | 28,780 | 8,075 | 257,350 | 9,490 |
| lb/Hr. | 338,170 | 338,170 | 64,150 | 273,990 | 224,290 | 1,361,380 | 49,540 |
| Phase | Vapor | Vapor | Liquid | Vapor | Liquid | Vapor | Vapor |

From the above results, it was calculated that the overall production of pure methanol was increased to 2613 MT/D, of which 1974 MT/D came from the gas phase loop and 629 MT/D from the liquid phase reactor. This represents a 24.5% increase in methanol production over the previous rate of 2100 MT/D for the stand-above gas phase loop. In addition, 11 MT/D of ethanol and higher alcohols would be produced.

Having thus described the present invention, what is now deemed appropriate for Letters Patent is set out in the following appended claims.

What is claimed is:

1. In a gas phase synthesis loop for the production of methanol from a syngas feed containing carbon dioxide and hydrogen, the improvement for increasing the capacity of methanol production which comprises:
   (a) passing said syngas feed, in a single pass, to a liquid phase methanol reactor to convert a portion of the syngas to methanol, thereby forming a methanol-containing syngas reactor effluent;
   (b) cooling said methanol-containing syngas reactor effluent to condense the methanol, thereby producing a first methanol stream and an unreacted syngas stream;
   (c) passing said unreacted syngas stream to a gas phase synthesis loop to produce a second methanol stream; and
   (d) recovering both the first and second methanol streams.

2. The process in accordance with claim 1 wherein said syngas feed is passed to a liquid phase methanol reactor to convert a portion of the syngas to methanol and higher aliphatic alcohols.

3. The process in accordance with claim 1 wherein said syngas feed is compressed to between 400 and 1200 psi prior to being passed to the liquid phase methanol reactor.

4. The process in accordance with claim 1 wherein said unreacted syngas stream is compressed to between 750 and 3000 psi prior to being passed to the gas phase synthesis loop.

5. The process in accordance with claim 1 wherein the syngas feed has a stoichiometric ratio $H_2/(CO+1.5\ CO_2)$ between 2 and 3.

6. The process in accordance with claim 1 wherein said liquid phase methanol reactor comprises an active methanol synthesis catalyst having average particle sizes ranging from 0.00002 to 0.25 inches suspended in an inert hydrocarbon liquid.

7. The process in accordance with claim 1 wherein the liquid phase methanol reactor is positioned intermediate to two stages of feed compression for the gas phase loop.

8. The process in accordance with claim 1 wherein the liquid phase methanol reactor is located subsequent to the last stage of feed compression for the gas phase synthesis loop.

9. The process in accordance with claim 1 wherein methanol production is increased by over 24% of the production rate of a stand-alone gas phase synthesis loop.

10. The process in accordance with claim 1 wherein the liquid phase methanol reactor has a ΔP for the syngas of less than 5 psi.

11. The process in accordance with claim 1 wherein the liquid phase methanol reactor temperature is between 150° C. and 400° C.

12. The process in accordance with claim 11 wherein the liquid phase methanol reactor temperature is between 230° C. and 250° C.

13. The process in accordance with claim 1 wherein the syngas feed is produced from the reforming of natural gas.

* * * * *